United States Patent [19]

Hirai et al.

[11] Patent Number: 4,530,991

[45] Date of Patent: Jul. 23, 1985

[54] LATENT CURING AGENTS FOR EPOXY RESINS

[75] Inventors: Kiyomiki Hirai, Kawasaki; Koji Takeuchi, Yokohama; Nobuo Ito, Oisomachi; Masahiro Abe, Kawasaki, all of Japan

[73] Assignee: Ajinomoto Co., Inc., Tokyo, Japan

[21] Appl. No.: 541,022

[22] Filed: Oct. 12, 1983

[30] Foreign Application Priority Data

Oct. 12, 1982 [JP] Japan ................. 57-178868

[51] Int. Cl.$^3$ .................. C08G 59/44; C07C 109/097
[52] U.S. Cl. .................. 528/123; 525/504; 528/327; 528/365
[58] Field of Search ............... 528/119, 123, 365, 327; 525/504; 564/151

[56] References Cited

U.S. PATENT DOCUMENTS

| | | |
|---|---|---|
| 2,847,395 | 8/1958 | Wear .............................. 528/365 X |
| 3,456,006 | 7/1969 | Aelony ............................ 528/123 X |
| 3,467,707 | 9/1969 | Aelony ............................ 528/365 X |
| 3,876,606 | 4/1975 | Kehr ................................... 523/457 |

*Primary Examiner*—Earl Nielsen
*Attorney, Agent, or Firm*—Oblon, Fisher, Spivak, McClelland & Maier

[57] ABSTRACT

Hydrazides of the formula (I) or (II)

$$N-CH_2CH_2CONHNH_2)_3 \quad (I)$$

$$(NH_2NHCOCH_2CH_2)_2N-R-N-CH_2CH_2CONHNH_2)_2 \quad (II)$$

are good latent curing agents for epoxy resin, in the formula (II) R is divalent hydrocarbon residue having 2-24 carbon atoms. The curing agents are useful in formulating novel storable one-package, heat-curable epoxy resin-based compositions.

7 Claims, No Drawings

LATENT CURING AGENTS FOR EPOXY RESINS

BACKGROUND OF THE INVENTION

1. Field of the Invention

The present invention relates to certain novel hydrazides and the use thereof as curing agents for epoxy resins.

2. Description of the Prior Art

Epoxy resins are widely employed as electric insulating materials, various moulded products, adhesives or coatings, because they give valuable cured resins having excellent mechanical, electrical and chemical properties when cured with suitable curing agents for example acid anhydride and amine curing agents. However, epoxy resin composition incorporating amine curing agents are cured rapidly at ordinary temperature and at elevated temperature and hence they lack storage stability. Also, epoxy resin composition incorporating acid anhydride curing agents are stable at ordinary temperature but heating for a long period of time at elevated temperature is required for full curing. Usually, tertiary amines, quaternary ammonium compounds or organo metal complexes are further added to the composition for the purpose of accelerating the curing rate. However, the addition of such cure accelerator impairs storage stability markedly.

There have been eagerly desired so-called latent curing agents which are compatible with epoxy resins to form a composition which is stable at relatively low temperature and which is rapidly cured when heated to an elevated temperature. Representative compounds which have been heretofore proposed as latent curing agents are dicyandiamide, dibasic acid hydrazide, boron trifluorideamine adduct, guanamine and melamine. Among these compounds, dicyandiamide, dibasic acid hydrazide and guanamine are useful in formulating epoxy resin compositions having excellent storage stability but full curing by means of these compound could be achieved only by heating at higher temperature than 150° C. for a long time. Also, boron trifluoride-amine adduct is hard to treat owing to its high hygroscopic property and it affects adversely the physical properties of the cured resin.

There has been heretofore almost no latent epoxy curing agent which was known to cause rapid curing at moderately elevated temperatures, that is 100° C.–150° C. and which gives an epoxy resin composition having excellent storage stability at ordinary temperatures.

SUMMARY OF THE INVENTION

The present invention provides novel hydrazide-type curing agents which are useful in making storable one-package curable epoxy resin compositions.

The present invention also provides hydrazide-type curing agents which alone or together with other curing agents can activate a rapid curing of an epoxy resin composition at relatively low temperatures and yet be extraordinarily resistant to gelling at 40° C. for three weeks or more.

The present invention also provides hydrazide-type curing agents which give cured epoxy resin having excellent transparency and flexibility.

DESCRIPTION OF THE INVENTION

The present invention provides as curing agents hydrazide compounds having the following general formulas (I) and (II)

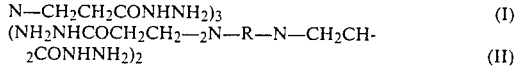

wherein R is a divalent hydrocarbon residue having 2–24 carbon atoms.

The hydrazides which may be represented by the above general formulas (I) or (II) are novel compounds and may be readily prepared by reacting an adduct of 1 mole of ammonia and 3 moles of alkyl acrylate having the general formula $CH_2=CHCOOR'$ wherein $R'$ is alkyl group or an adduct of 1 mole of diamine represented by the general formula $NH_2-R-NH_2$ wherein R has the meanings set forth above and 4 moles of alkyl acrylate, with hydrazine hydrate. The adduct of ammonia and trimolecular alkyl acrylate, and the adduct of diamine and tetramolecular alkyl acrylate being represented by the following general formula (a) and (b), respectively.

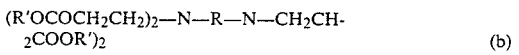

wherein R has the meanings set forth above and $R'$ is an alkyl group having 1–4 carbon atoms.

Examples of diamines which may be represented by the general formula $NH_2-R-NH_2$ wherein R has the meanings set forth above and which may be employed as the raw material for the preparation of the hydrazide of the general formula (II) include ethylene diamine, propylene diamine, trimethylenediamine, tetramethylenediamine, pentamethylenediamine, hexamethylenediamine, octamethylenediamine, nonamethylenediamine, decamethylenediamine, dodecamethylene diamine, 1,3-diamino-2,2-dimethylpropane, 1,2-cyclohexanediamine, 1,3-di(aminomethyl)cyclohexane, 4,4'-diaminodicyclohexylmethane and the like.

The preparation of the ammonia-trimolecular alkyl acrylate adduct (a) may be accomplished by heating an 28% concentrated aqueous ammonia solution and alkyl acrylate at about 40° C. for several hours under stirring, the amount of alkyl acrylate being at least 3 times mole based on ammonia.

The preparation of the diaminetetramolecular alkyl acrylate adduct (b) may be accomplished by reacting 1 mole of diamine with at least 4 moles of alkyl acrylate at 0°–40° C. for several hours under stirring.

The alkyl acrylate to be reacted with ammonia or diamine is not particularly limited. Usually a lower alkyl ester of 1–4 carbon atoms is employed. Especially, methyl ester is practical. After the addition reaction has been completed, the excess acrylic ester is removed from the reaction mixture by distillation.

The thus obtained ammonia-trimolecular acrylic ester adduct (a) or the diamine-tetramolecular acrylic ester adduct (b) obtained is further reacted with hydrazine hydrate in a methanol solvent at room temperature for several hours under stirring. The amount of hydrazine hydrate may be at least 3 times mole based on the adduct (a) while it may be at least 4 times mole based on the adduct (b). The reaction may be carried out at 40°–50° C. if necessary.

After the completion of the reaction, the excess hydrated hydrazine and the solvent are removed from the reaction mixture by distillation and the precipitated hydrazide is separated and recrystallized from a suitable solvent such as methanol, ethanol or water. The hydrazide of the present invention may be pulverized into fine particles.

The hitherto known dibasic acid hydrazides such as adipic acid hydrazide, sebacic acid hydrazide, isophthalic acid hydrazide and the like are high melting compound above 180° C. and the epoxy resin compositions incorporating such dibasic acid hydrazides is cured when heated to 150° C. or higher temperatures. Contrary thereto, the hydrazides of the present invention are relatively low melting compounds and provide when incorporated into an epoxy resin, curable compositions which are stable for periods of several weeks at 40° C. and which can thereafter be readily cured at temperatures of as low as about 100°-140° C. to give colorless, transparent and tough cured product. Especially, the use of hydrazide derived from the higher aliphatic straight chain diamine having 10 to 24 carbon atoms imparts excellent flexibility to the cured resin.

The required amount of curing agent is determined by the number of active hydrogen atoms in the curing agent employed and the number of epoxy groups in the epoxy resins. In general, 0.5–1.5 preferably 0.7–1.2 active hydrogen equivalent weight per epoxy equivalent weight is employed.

As epoxy resins which may be applied to the hydrazide curing agents of the present invention, various well-known ones having an average of more than 1 epoxy groups in the molecule may be employed. Representative epoxy resins are those based on glycidyl ethers of polyhydric phenols such as 2,2-bis(4-hydroxyphenyl)-propane (Bisphenol A), resorcinol, hydroquinone, pyrocatechol, saligenin, glycidyl ether of Bisphenol F and glycidyl ether of phenolformaldehyde resin.

If necessary, other curing agents, cure accelerator and fillers may be employed in combination with the curing agent of the present invention.

The following examples illustrate the preparation of the hydrazides of the present invention.

EXAMPLE 1

Preparation of N—CH$_2$CH$_2$CONHNH$_2$)$_3$  (1)

In an autoclave equipped with electromagnetic stirrer, 43 g of methyl acrylate and 9 g of 28% aqueous ammonia were mixed. The mixture was heated to 60° C. for 3 hours with stirring. After cooling, the reaction mixture was dissloved in 150 ml of ethyl ether. After washing three times with 100 ml of water, ethyl ether and the unreacted methyl acrylate were removed under the reduced pressure. The residue was fractionated under reduced pressure to obtain 16.3 g of the adduct (1)′. 131.5°~132.5° C. (1 mmHg).

N—CH$_2$CH$_2$COOCH$_3$)$_3$  (1)′

15.5 of the adduct (1)′ was dissolved in 50 ml of ethanol. To this solution, 12.0 g of 80% hydrazine hydrate solution was added and was allowed to react at 40° C. for 1.5 hours with stirring. From the reaction mixture, excess hydrazine hydrate and ethanol were removed in vacuo. The residue was dissolved in 10 ml of ethanol and allowed to stand overnight to precipitate the crystals. After filtration, the crystals were recrystallized from ethanol, dried in vacuo to obtain 8.0 of prisms.

The analytical values were as shown below.

Melting point 129° C.

Elemental analysis:

|  | C | H | N (%) |
|---|---|---|---|
| Found | 39.34 | 7.87 | 35.71 |
| Calculated for C$_9$H$_{21}$N$_7$O$_3$ | 39.26 | 7.69 | 35.62 |

NMR spectrum (D$_2$O/DSS):

β (ppm)

2.36 (6H, t, CH$_2$CO)

2.81 (6H, t, CH$_2$N)

Field desorption mass spectrum:

[M+H]$^+$ at m/e 276.

EXAMPLE 2

Preparation of

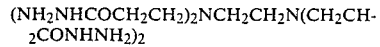
(NH$_2$NHCOCH$_2$CH$_2$)$_2$NCH$_2$CH$_2$N(CH$_2$CH$_2$CONHNH$_2$)$_2$  (2)

To a mixture of 6.0 g of ethylene diamine and 10 ml of methanol contained in a 300 ml three-necked flask equipped with stirrer was added dropwise 105 g of methyl acrylate with stirring at room temperature.

After dropping, the reaction mixtures was allowed to stand overnight. Methanol and excess methyl acrylate were removed in vacuo to obtain 39.9 g of the adduct (2)′.

(CH$_3$OCOCH$_2$CH$_2$)$_2$N—CH$_2$CH$_2$—N(CH$_2$CH$_2$COOCH$_3$)$_2$  (2)′

39.5 g of the adduct (2)′ thus obtained and 27.3 g of 80% hydrazine hydrate solution were dissolved in 150 ml of methanol, and the solution was heated under reflux for 4 hours with stirring. From the reaction mixture, excess hydrazine hydrate and methanol were removed in vacuo. The residue was dissolved in 50 ml of methanol and allowed to stand overnight to precipitate the crystals. After filtration, the crystals were washed with methanol, dried under reduced pressure to obtain 32.3 g of the target product.

The analytical values were as shown below.

Melting point: 126°~127° C.

Elemental analysis:

|  | C | H | N (%) |
|---|---|---|---|
| Found | 41.56 | 8.31 | 34.24 |
| Calculated for C$_{14}$H$_{32}$N$_{10}$O$_4$ | 41.58 | 7.92 | 34.65 |

EXAMPLE 3

Preparation of

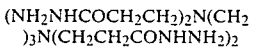
(NH$_2$NHCOCH$_2$CH$_2$)$_2$N(CH$_2$)$_3$N(CH$_2$CH$_2$CONHNH$_2$)$_2$  (3)

To a mixture of 7.4 g of 1,3-diaminopropane and 70 ml of methanol contained in a 300 ml three-necked flask equipped with stirrer was added dropwise 41.3 g of methyl acrylate with stirring at room temperature. After dropping, the mixture was stirred for 4 hours at room temperature. Methanol and excess methyl acrylate were removed in vacuo to obtain 41.1 g of the adduct (3)′.

(CH₃OCOCH₂CH₂)₂N(CH₂)₃N(CH₂CH₂COOCH₃)₂     (3)′

41.1 g of the adduct (3)′ thus obtained and 30.0 g of 80% hydrazine hydrate solution were dissolved in 100 ml of methanol, and the solution was stirred for 5 hours at room temperature. From the reaction mixture, excess hydrazine hydrate and methanol were removed in vacuo. The residue was allowed to stand overnight to precipitate the white crystals. After filtration, the crystals were recrystallized from ethanol, dried in vacuo to obtain 29.3 g of the target product.

The analytical values were as shown below.
Melting point 95° C.
Elemental analysis:

|  | C | H | N (%) |
|---|---|---|---|
| Found | 42.95 | 8.60 | 33.22 |
| Calculated for C₁₅H₃₄N₁₀O₄ | 43.05 | 8.19 | 33.47 |

27.0 g of the adduct (4)′ thus obtained and 15.0 g of 80% hydrazine hydrate solution were dissolved in 100 ml of methanol. The solution was stirred for 3 hours at room temperature to obtain white crystals. After filtration, the crystals were recrystallized from the mixture of water and methanol (2:8), washed with methanol, dried under reduced pressure to obtain 25.5 g of the target product.

The analytical values were as shown below.
Melting point: 129° C.
Elemental analysis:

|  | C | H | N (%) |
|---|---|---|---|
| Found | 52.74 | 10.01 | 25.48 |
| Calculated for C₂₄H₅₂N₁₀O₄ | 52.91 | 9.62 | 25.72 |

The hydrazides prepared by similar manner as in Examples, their melting points, the solvents for recrystallization and the values of elemental analysis are shown in Table 1.

TABLE 1

| Sample No. | Hydrazides | Solvent for recrystallization | Melting point (°C.) | Elemental analysis (calculated) | | |
|---|---|---|---|---|---|---|
|  |  |  |  | C % | H % | N % |
| 1 | N—(CH₂CH₂CONHNH₂)₃ | ethanol | 129 | 39.34 (39.26) | 7.87 (7.69) | 35.71 (35.62) |
| 2 | (NH₂NHCOCH₂CH₂)₂N(CH₂)₂N(CH₂CH₂CONHNH₂)₂ | methanol | 126~127 | 41.56 (41.58) | 8.31 (7.92) | 34.24 (34.65) |
| 3 | (NH₂NHCOCH₂CH₂)₂NCHCH₂N(CH₂CH₂CONHNH₂)₂ with CH₃ group | ethanol | 131 | 42.91 (43.05) | 8.58 (8.19) | 33.27 (33.47) |
| 4 | (NH₂NHCOCH₂CH₂)₂N(CH₂)₃N(CH₂CH₂CONHNH₂)₂ | ethanol | 95 | 42.95 (43.05) | 8.60 (8.19) | 33.22 (33.47) |
| 5 | (NH₂NHCOCH₂CH₂)₂N(CH₂)₆N(CH₂CH₂CONHNH₂)₂ | methanol | 111 | 46.73 (46.94) | 9.05 (8.75) | 30.04 (30.41) |
| 6 | (NH₂NHCOCH₂CH₂)₂N(CH₂)₁₂N(CH₂CH₂CONHNH₂)₂ | water, methanol (2:8) | 129 | 52.74 (52.91) | 10.01 (9.62) | 25.48 (25.72) |

EXAMPLE 4

Preparation of (NH₂NHCOCH₂CH₂)₂N(CH₂)₁₂N(CH₂CH₂CONHNH₂)₂     (4)

To a mixture of 10.0 g of 1,12-diaminododecane and 100 ml of methanol contained in a 300 ml three-necked flask equipped with stirrer was added dropwise 22.4 g of methyl acrylate with stirring at room temperature.

After dropping, the reaction mixture was stirred for 5 hours at room temperature. Methanol and excess methyl acrylate were removed in vacuo to obtain 27.0 g of the adduct (4)′.

(CH₃OCOCH₂CH₂)₂N(CH₂)₁₂N(CH₂CH₂COOCH₃)₂     (4)′

EXAMPLE 5

Reactivity and storage stability of the formulated epoxy resin composition were evaluated.

1. Preparation of the sample

The formulation of the sample is shown in Table 2. The individual components were sufficiently mixed in a mortar.

2. Evaluation of the reactivity (2-1) Onset temperature and peak temperature were measured by differential thermal analysis (DTA)
  Sample weight: about 10 mg
  Standard material: α-Al₂O₃
  Heating rate: 5° C./min.

(2-2) The sample was put into a Geer's oven for 60 minutes and cured temperature was measured.

3. Storage stability

The sample was put into a Geer's oven set to 40° C. and the day required for the sample becoming non-fluidity was measured.

The results obtained are summarized in Table 3.

TABLE 2

| | | Formulation No. | | | | | | | | |
|---|---|---|---|---|---|---|---|---|---|---|
| | | 1 | 2 | 3 | 4 | 5 | 6 | 7 | 8 | 9 |
| The present | Epon 828*¹ | 100 | 100 | 100 | 100 | 100 | 100 | 100 | 100 | 100 |
|  | Compound (1) | 23 | | | | | | | | |

TABLE 2-continued

|  |  | Formulation No. | | | | | | | | |
|---|---|---|---|---|---|---|---|---|---|---|
|  |  | 1 | 2 | 3 | 4 | 5 | 6 | 7 | 8 | 9 |
| invention | Compound (2) |  | 27 |  |  |  |  |  |  |  |
|  | Compound (3) |  |  | 28 |  |  |  |  |  |  |
|  | Compound (4) |  |  |  | 28 |  |  |  |  |  |
|  | Compound (5) |  |  |  |  | 30 |  |  |  |  |
|  | Compound (6) |  |  |  |  |  | 36 |  |  |  |
| Control | Adipic dihydrazide |  |  |  |  |  |  | 23 |  |  |
|  | Isophthalic dihydrazide |  |  |  |  |  |  |  | 26 |  |
|  | Dicyandiamide |  |  |  |  |  |  |  |  | 8 |

*[1] A product of Shell Chemical Co. bisphenol A type epoxy resin having epoxy equivalent of 175–210.

TABLE 3

|  | Formulation No. | Reactivity | | | Storage stability (40° C.) |
|---|---|---|---|---|---|
|  |  | Onset temp. | Peak temp. | Cured temp. (60 min) |  |
| The present invention | No. 1 | 118° C. | 130° C. | 100° C. | >2 weeks |
|  | No. 2 | 130 | 155 | 120 | " |
|  | No. 3 | 131 | 152 | 110 | " |
|  | No. 4 | 120 | 152 | 130 | " |
|  | No. 5 | 109 | 147 | 100 | " |
|  | No. 6 | 130 | 152 | 110 | " |
| Control | No. 7 | 151 | 173 | 160 | " |
|  | No. 8 | 158 | 192 | 160 | " |
|  | No. 9 | 160 | 199 | 180 | (Partial separation occurred) |

The result of Table 3 shows that the latent curing agent for epoxy resin in this invention has excellent storage stability and reactivity. Especially, the reactivity of this agent is superior to the control agent.

What we claim is:

1. A compound having the formula (I) or (II):

$$N-CH_2CH_2CONHNH_2)_3 \quad (I)$$

$$(NH_2NHCOCH_2CH_2-)_2N-R-N-CH_2CH_2CONHNH_2)_2 \quad (II)$$

wherein R is a divalent hydrocarbon residue having 2–24 carbon atoms.

2. A compound claimed in claim 1, wherein R is $-(CH_2)_{12}-$.

3. A curable epoxy resin composition comprising (a) an epoxy resin having an average of more than one epoxy group per molecule and (b), as curing agent, a compound having the formula (I) or (II):

$$N-CH_2CH_2CONHNH_2)_3 \quad (I)$$

$$(NH_2NHCOCH_2CH_2-)_2N-R-N-CH_2CH_2CONHNH_2)_2 \quad (II)$$

wherein R is a divalent hydrocarbon residue having 2–24 carbon atoms.

4. The curable epoxy resin composition claimed in claim 3, wherein the amount of said compound is enough to provide 0.5–1.5 times active hydrogen equivalent weight based on epoxy equivalent weight.

5. The curable epoxy resin composition claimed in claim 3, wherein R is $-(CH_2)_{12}-$.

6. The curable epoxy resin composition claimed in claim 3, wherein said epoxy resin is polyglycidyl ether of polyhydric phenol.

7. A cured resin obtained by contacting an epoxy resin having an average of more than 1 epoxy group per molecule with as curing agent a compound having the formula (I) or (II):

$$N-CH_2CH_2CONHNH_2)_3 \quad (I)$$

$$(NH_2NHCOCH_2CH_2-)_2N-R-N-CH_2CH_2CONHNH_2)_2 \quad (II)$$

wherein R is a divalent hydrocarbon residue having 2–24 carbon atoms, the amount of said compound being enough to provide 0.5–1.5 times active hydrogen equivalent weight based on epoxy equivalent weight.

* * * * *